United States Patent [19]
Uragami et al.

[11] Patent Number: 5,271,846
[45] Date of Patent: * Dec. 21, 1993

[54] METHOD FOR SEPARATING A LIQUID COMPONENT FROM A SOLUTION CONTAINING TWO OR MORE LIQUID COMPONENTS

[75] Inventors: Tadashi Uragami, Mino; Yoshiaki Tanaka, Takaishi, both of Japan

[73] Assignee: Lignyte Co., Ltd., Osaka, Japan

[ * ] Notice: The portion of the term of this patent subsequent to Jan. 28, 2008 has been disclaimed.

[21] Appl. No.: 856,797

[22] Filed: Mar. 24, 1992

Related U.S. Application Data

[63] Continuation-in-part of Ser. No. 363,021, Jun. 8, 1989, abandoned, which is a continuation of Ser. No. 255,304, Oct. 11, 1988, Pat. No. 5,006,255, which is a continuation of Ser. No. 130,504, Dec. 9, 1987, Pat. No. 4,983,303.

[30] Foreign Application Priority Data

Mar. 25, 1991 [JP] Japan .................. 3-59863
Mar. 25, 1991 [JP] Japan .................. 3-59864

[51] Int. Cl.⁵ ............................................. B01D 61/36
[52] U.S. Cl. ...................................... 210/640; 210/406
[58] Field of Search ............... 210/640, 406; 203/19, 203/91; 55/16, 158, 159

[56] References Cited

U.S. PATENT DOCUMENTS 4,978,430 12/1990 Nakagawa .................. 203/14
4,983,303 1/1991 Uragami .................. 203/91 X

FOREIGN PATENT DOCUMENTS 0273267 7/1988 European Pat. Off. .
0346739 12/1989 European Pat. Off. .
851048 7/1952 Fed. Rep. of Germany .

*Primary Examiner*—Frank Spear
*Attorney, Agent, or Firm*—Armstrong, Westerman, Hattori, McLeland & Naughton

[57] ABSTRACT

An improved method for separating a particular liquid component from a solution containing two or more liquid components. The method employs a vessel divided into a solution chamber and a vacuum chamber by a permeable membrane which is a porous membrane exhibiting a superior affinity to the particular component intended to be separated than to the other components. The solution is placed in the solution chamber out of direct contact with the permeable membrane at which condition a vacuum is applied to the vacuum chamber to evaporate the solution in the chamber and draw the resulting vapors through the permeable membrane into the vacuum chamber, thereby collecting the particular component from the solution in a vapor-to-vapor permeation through the permeable membrane.

6 Claims, 2 Drawing Sheets

METHOD FOR SEPARATING A LIQUID COMPONENT FROM A SOLUTION CONTAINING TWO OR MORE LIQUID COMPONENTS

The present application is a continuation-in-part of application Ser. No. 07/363,021, filed Jun. 8, 1989, and now abandoned, which in turn is a continuation of application Ser. No. 07/255,304, filed Oct. 11, 1988 and now U.S. Pat. No. 5,006,255, which in turn is a continuation of application Ser. No. 07/130,504, filed Dec. 9, 1987 and now U.S. Pat. No. 4,983,303.

BACKGROUND OF THE INVENTION

1. Field of the Invention

The present invention relates to a method for separating a liquid component from a solution containing two or more liquid components through the use of a permeable membrane, and more particularly to an improved method of separating the component in vapor-to-vapor permeation environment.

2. Description of the Prior Art

As a method of separating a particular liquid component from a solution or mixture such as an organic liquid containing two or more liquid components there has been developed a pervaporation (permeation evaporation) method. The principle of the permeation method utilizes a separation vessel divided into an upper solution chamber and a lower vacuum chamber by means of a permeable membrane. By reducing a pressure in the vacuum chamber while keeping the solution introduced into the solution chamber in contact with the membrane, a particular component in the liquid solution will permeate and diffuse through the permeable membrane selectively in preference to the other components so that the component to be separated selectively permeates through the membrane and evaporate from the surface of the permeable membrane into the vacuum chamber. In this permeation method, however, because of that the liquid solution is kept in direct contact with the permeable membrane to effect the permeation in a liquid-to-vapor phase environment, there arises a serious problem that the permeable membrane which is generally made from a macromolecular material is likely to be swelled due to the direct contact with the solution. When the permeable membrane is swelled, its permeability will be considerably degraded to thereby lower the separation efficiency to an unacceptable level.

To overcome the above problem, the inventor has proposed in U.S. patent application Ser. No. 130,504 [U.S. Pat. No. 4,983,303] and Ser. No. 363,021 an evapomeation (evaporation permeation) method which is directed to effect the permeation in vapor-to-vapor phase environment. That is, as schematically shown in FIG. 1, the evapomeation method utilizes a like vessel 10 divided into a lower solution chamber 12 and an upper vacuum chamber 13 by a non-porous permeable membrane 14 and effects the permeation separation while keeping the solution S from which a particular component is to be separated out of contact with the permeable membrane 14. Thus, the vapors of the particular component will selectively permeate through the membrane 14 in a vapor phase into the vacuum chamber 13 when drawn by vacuum through the membrane 14. With this result, the evapomeation method can be free from the swelling which is seen in the conventional pervaporation method and therefore prevents a lowering in separation efficiency. Nevertheless, the evapomeation method may be found insufficient due to limited separation efficiency inherent to the permeable membrane employed. That is, since the separation relies upon diffusion permeation of the component into the membrane which occurs only at a relatively slow rate, it is not expected to separate the liquid components at a high rate sufficient for industrial application.

SUMMARY OF THE INVENTION

The present invention eliminates the above problems and provides an improved permeation separation method for further enhancing separation efficiency. The method of the present invention utilizes a vessel which is divided by a permeable membrane into a solution chamber and a vacuum chamber. The solution is placed in the solution chamber out of direct contact with the permeable membrane. Then, a vacuum is applied to the vacuum chamber to evaporate the solution in the solution chamber and draw the resulting vapors through the permeable membrane into the vacuum chamber, whereby the components to be separated selectively through the membrane in a vapor-to-vapor phase environment. The characterizing feature of the present invention resides in that the permeable membrane is a porous membrane which exhibits an affinity stronger to the particular liquid components intended to be separated than to the other components. With this technique, it is readily possible to remarkably increase the separation rate up to an industrially practical level. Such a high separation rate is attributed to the fact that the particular liquid component to be separated enters minute pores in the membrane readily due to its strong affinity to the membrane, while the other liquid components exhibit less affinity to the membrane and enter with difficulty into the minute pores of the membrane. The particular liquid component entering the minute pores are aided in their passage through the membrane by means of the vacuum applied from the vacuum chamber. Therefore, the particular liquid component is separated at an increased rate which is far greater than that expected in the prior evapomeation method relying upon the diffusion permeation of the component into the non-porous membrane.

Accordingly, it is a primary object of the present invention to provide an improved permeation separation method which is capable of separating a particular liquid component from a solution containing two or more liquid components at such a remarkably increased separation rate sufficient as to ensure industrial practicability.

While applying the vacuum through the membrane for separation of the particular component, a suitable gas may be introduced into the solution chamber for enhancing the separation and therefore further increasing the separation efficiency, which is therefore another object of the present invention.

The affinity is determined by a critical surface tension and can be said stronger to the particular liquid component than to the others when the critical surface is closer to a surface tension of the particular liquid component than to those of the others. In the preferred embodiment, the permeable membrane is selected to have a critical surface tension which is greater than a surface tension of the particular component to be separated and is less than those of the other components. Preferably, the membrane is formed to have the pores of $1 \times 10^{-3}$ to 5 $\mu$m in average diameter and have a porosity of at least 5%.

When separating the particular component having a lower boiling temperature than those of the other liquid components, it is mostly preferred to cool the membrane while heating the solution in the solution chamber in order to increase the separation ratio. This is because that when reaching a cooled zone adjacent to the permeable membrane the vapors of the components having a higher boiling point are likely to aggregate than that of the intended component having a lower boiling point to thereby form a greater aggregation of molecules which is difficult to enter the pores of the membrane or even cause to return back to the liquid phase. Thus, the vapors of the intended component having the lower boiling point are allowed to preferentially enter or permeate through the membrane while those of the other components are rejected so that the vapors of the intended component can be collected at a greater concentration or efficienty in the vacuum chamber than those of the components not intended.

It is therefore a further object of the present invention to provide an improved permeation separation method which is capable of separating the particular liquid component having a lower boiling point than the other components at an increased separation efficiency.

The above and other objects and advantages of the present invention will become more apparent from the following description of the invention with reference to the attached drawings.

DETAILED DESCRIPTION OF THE INVENTION

Figure 1:
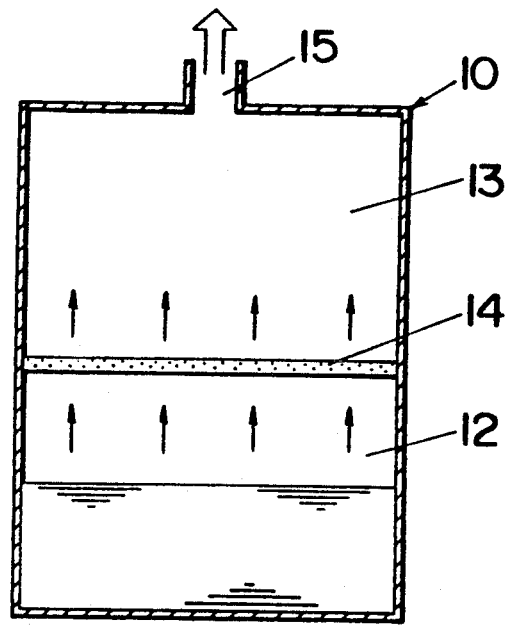
FIG. 1 is a schematic view illustrating a basic concept of the evapomeation separation method.

Referring to FIG. 1 which illustrates the principle of the "evapomeation (evaporation permeation)" separation method of the present invention, a separation vessel 10 is divided by means of a permeable membrane 14 into a lower solution chamber 12 and an upper vacuum chamber 13. A solution S, for example, an organic solution containing two or more volatile or evaporizable components is introduced into the solution chamber 12 and is kept out of direct contact with the permeable membrane 14. As shown in detail in FIG. 2, the vacuum chamber 13 is provided with a port 15 which is connected to a source of vacuum such as a vacuum pump for evacuating the vacuum chamber and in turn for evaporating the solution S in the solution chamber 12 and drawing the resulting vapors through the permeable membrane 14. The vapors permeating through the membrane 14 into the vacuum chamber 13 is collected or recovered by a suitable manner. Projecting into the solution chamber 12 is a pipe 20 with a valve 21 for supplying a suitable gas, for example, air, nitrogen or the like into the solution chamber 12 above the liquid level of the solution S. The solution is, for example, an aqueous solution of alcohol, in which case alcohol concentration can be increased by selectively permeate the alcohol in preference to the water. The present invention is not limited to the separation of the water-alcohol solution and can be widely utilized for separation of a particular liquid component from a solution containing two or more liquid components. Since the permeable membrane 14 allows a particular component to selectively permeate in preference to the others, it is readily possible to complete the separation either by collecting the component having passed into the vacuum chamber 13 through the permeable membrane 14 or by collecting the remaining solution in the solution chamber 12 from which the particular component has been removed.

The permeable membrane 14 utilized in the present invention is a porous membrane exhibiting a stronger affinity to the particular liquid component intended to be separated than to the other liquid component or components contained in the solution. That is, the membrane 14 is selected to have a critical surface tension $\gamma_C$ which is closer to the particular liquid component than to the other component or components in the solution. The term "critical surface tension" is defined to be equal to a surface tension $\gamma_L$ of a liquid with respect to the solid surface, in this instance, the surface of the membrane when contact angle $\theta$ is 0 ($\cos\theta = 1$), and can be well indicative of wettability of a specific membrane to the liquid components so that the membrane can be said to be readily wetted by or have a strong affinity to a particular liquid component when the critical surface tension $\gamma_C$ is closer to or greater than the surface tension of that liquid component than that of the other liquid component or components contained in the solution. For example, when separating the particular liquid component A from a solution containing other liquid components B, C, and so on, the membrane is selected to have a critical surface tension $\gamma_C$ which is closer to the surface tension $\gamma_L$ of the particular liquid component than to those of the other components B, C, and so on. Preferably, the membrane is selected to have a critical surface tension $\gamma_C$ which is greater than the surface tension $\gamma_L$ of the particular liquid component A and at the same time less than those of the other liquid components B, C, and so on.

Table 1 shows surface tension of several liquid components which may form a liquid solution from which a particular component is to be separated through the membrane. For instance, when the membrane is selected to have critical surface tension $\gamma_C$ which is closer to surface tension $\gamma_L$ of water than those to the other listed components, water can be separated from the other listed components. When the membrane is selected to have critical surface tension $\gamma_C$ which is between surface tension $\gamma_L$ of the water and that of another listed component, the separation between the water and another component can be made efficiently.

TABLE 1

| Component | Surface tension (dyne/cm) |
|---|---|
| ethylether | 17.0 |
| ethanol | 22.6 |
| acetone | 23.3 |
| ethyl acetate | 23.8 |
| tetrahydrofuran | 26.4 |
| carbon tetrachloride | 26.8 |
| toluene | 28.4 |
| benzene | 28.9 |
| methyl cellosolve | 35.0 |
| dimethyl formaldehyde | 35.2 |
| propylene carbonate | 40.8 |

TABLE 1-continued

| Component | Surface tension (dyne/cm) |
|---|---|
| water | 72.8 |

The membrane 14 may be fabricated from, although not limited to, polypropylene, polytetrafluoroethylene, poly carbonate, and the like to be a porous membrane having a porosity of 5% or more and formed with minute pores having an average diameter of $1 \times 10^{-3}$ to 5 $\mu$m. For example "Celguard" or "Duraguard" from Hoechst Corp. is available as polypropylene membrane, "Fluoropore" from Sumitomo Denko K. K. is available as the polytetrafluoroethylene membrane, and "Nucleipore" from Nucleipore Corp. is available as the polycarbonate membrane. The minute pores may not be strictly circular and may be of various non-circular configuration. In this sense the diameter of the pores is determined as that of a circular pore having an equivalent opening area to that of the non-circular pore. Above 5 $\mu$m of the average pore diameter, the membrane will pass the particular liquid component and the other liquid components together, failing to selectively permeate the particular liquid component. Below $1 \times 10^{-3} \mu$m of the average pore diameter, the other hand, the particular component is reluctant to pass through the pores to thereby lower separation rate down to a practically unacceptable level. Further, below 5% of porosity the membrane is expected to permeate only a limited amount of the particular liquid component per unit time, making it difficult to obtain good separation rate of a practically acceptable level.

Turning back to FIG. 2, when the vacuum chamber 13 is evacuated through the port from the vacuum pump, the vacuum is applied also to the solution chamber 12 through the membrane 14 to thereby evaporate the solution and feed the vapors of the liquid components of the solution to reach the membrane 14. At this condition, the membrane 14 exhibits a stronger affinity to a particular liquid component having surface tension $\gamma_L$ closer to the critical surface tension $\gamma_C$ of the membrane than to the other liquid components so that the membrane 14 is wetted with that particular liquid component while substantially rejecting the other liquid component. Particularly, the membrane 14 is wetted substantially only with the particular liquid component having surface tension $\gamma_L$ less than the critical surface tension $\gamma_C$ of the membrane 14 while rejecting the other component having surface tension $\gamma_L$ greater than the critical surface tension $\gamma_C$ of the membrane 14. Accordingly, only the liquid component having the surface tension $\gamma_L$ closer to and less than the critical surface tension $\gamma_C$ of the membrane 14 is allowed to proceed through the minute pores of the membrane 14 into the vacuum chamber 13, while the other components having surface tension $\gamma_L$ which is far away from and greater than the critical surface tension $\gamma_C$ are rejected by the membrane 14 and substantially inhibited from passing through the pores of the membrane 14 into the vacuum chamber 13. In this manner, the particular liquid component having surface tension $\gamma_L$ closer to and less than the critical surface tension $\gamma_C$ can be separated through the membrane and can be collected in an increased concentration from the vacuum chamber. The other liquid components can be collected from the solution chamber 12, when required. The separation through the permeable membrane 14 with the minute pores in accordance with the present invention can be effected at an increased rate far greater than the prior evapomeation separation method relying upon the non-porous permeable membrane as proposed in the prior U.S. patent applications Ser. No. 130,504 (U.S. Pat. No. 4,983,303) and Ser. No. 363,021.

It should be noted here that during the operation of permeating the particular liquid component through the membrane 14, it is preferred to supply a suitable gas, for example, air or nitrogen by way of pipe 20 into the solution chamber 12 for improving separation efficiency or enhancing the concentration of the component separated from the solution. Although not clear, such increased separation rate is assumed to result from the followings. The gas supplied into the solution chamber 12 is drawn into the vacuum chamber 13 through the minute pores of the membrane 14 due to the vacuum being applied to the vacuum chamber 13. Since the molecules of the gas is far smaller than those of the vapors of the liquid components, the gas is readily fed through the membrane in preference to the liquid components to thereby leave the liquid components accumulated in the vicinity of the membrane. Whereby the liquid components can have more chances to be in contact with the membrane 14 and are therefore subjected sufficiently to the above separation mechanism due to the difference between the critical surface tension $\gamma_C$ and the surface tension $\gamma_L$ of the liquid components. Anyhow, the concentration of the liquid component can be increased by supplying a suitable gas into the solution chamber 12 at the time of applying the vacuum through the membrane 14. Although the separation efficiency or the concentration can be increased with the increase in the supplying amount of the gas, the separation rate will decrease correspondingly to eventually lower the separation efficiency. Therefore, it is required to choose the supplying amount of the gas per unit time for well balancing the concentration of the separated liquid component and the separation rate for optimum separation efficiency.

Figure 2:
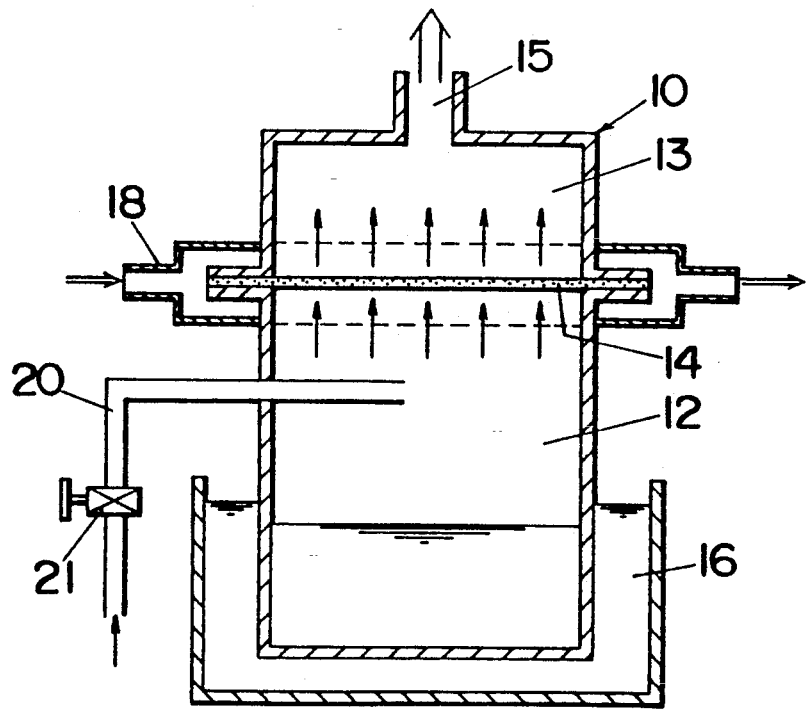
FIG. 2 is a schematic view of an apparatus employed in the present invention for illustrating a separation method in accordance with a preferred embodiment of the present invention.

When separating a liquid solution containing two or more liquid components having different boiling points, for example an aqueous solution of ethanol (boiling point of which is 78.3° C.) or of methanol (boiling point of which is 64.1), it is preferred to heat the solution S in the solution chamber and at the same time to cool the membrane 14 to provide a considerable temperature difference therebetween in order to separate a particular liquid component having a lower boiling point from the solution. For this purpose, the solution chamber 12 is surrounded by a heating bath 16, as shown in FIG. 2. The heating of the solution S may be effected alternatively by providing a heating jacket around the solution chamber 12, providing an immersion heater in the solution chamber 12, or the like heating device. The heating of the solution S, in the present invention, means to heat the solution S to a temperature above that of an environment or room temperature. 14. A cooling jacket 18 is provided to surround the permeable membrane 14 in order to cool the membrane 14 by a cooling medium continuously fed through the jacket 18. In this case, the membrane 14 is selected to be capable of permeating the particular component of the lower boiling point in preference to the other. That is, the membrane 14 has a critical surface tension $\gamma_C$ which is closer to a surface tension $\gamma_L$ of the particular component having the lower boiling point than to that of the other component and at the same time which is greater than the surface tension $\gamma_L$ of the particular component having the lower boiling point and less than that of the other component $\gamma_L$.

When applying the vacuum through the membrane 14 while cooling the membrane 14 and heating the solution S, the vapors of the component having a lower boiling point than the other reach the membrane in a greater concentration than the other due to the difference of the boiling points and are allowed to pass through the membrane 14 in preference to the other as the membrane 14 is readily wetted with the liquid component having the lower boiling point rather than the other component. Thus, the component having the lower boiling point are drawn into the vacuum chamber 13 in preference to the other. For example, the vapors of ethanol or methanol having a lower boiling point than water are caused to permeate through the membrane in preference to the water, to thereby increase ethanol or methanol concentration within the vacuum chamber 13. By cooling the permeable membrane 14 while heating the solution S, a more enhanced separation could result. The exact reason or mechanism for such enhanced separation is not known, but it is assumed that the vapors of the components having a higher boiling point are most likely to aggregate when reaching adjacent the cooled membrane and return to liquid or at least form a large sized aggregation which is difficult to permeate through the membrane, thus enabling substantially only the vapors of the component having a lower boiling point to permeate through the membrane. Since the membrane 14 is constantly exposed to the vapors of the solution, the membrane is correspondingly heated to reduce the above cooling effect. Nevertheless, the gas being supplied into the solution chamber 12 and feed through the membrane 14 can act to cool or cancel the heating by the vapors, thereby maintaining the enhanced separation efficiency through the membrane 14. It should be noted at this time that, although the apparatus of FIG. 2 is designed to cool the permeable membrane 14 and therefore the adjacent zones on the opposite sides thereof, the cooling could be limited only to the zone adjacent the solution side of the permeable membrane 14 for achieving the above enhanced separation, and the cooling is not necessarily made to the opposite zone in the vacuum chamber or the permeable membrane itself. Therefore, any other cooling scheme or means could be utilized to effect such limited cooling while retaining the equally enhanced separation.

The present invention will be discussed with reference to the following examples, which are provided by way of illustration and not by way of limitation. All percent and parts are by weight.

EXAMPLE 1

A 10 wt % aqueous solution of ethanol was separated by the use of a 25 μm thick porous permeable membrane of polypropylene which is available from Hoechst Corp. under the tradename of "Duraguard #2400" and has a critical surface tension 35 dyne/cm with a porosity of 38%. The membrane has evenly distributed minute elliptic pores having a major diameter of 0.125 μm and a minor diameter of 0.05 μm with an average diameter of 0.079 μm. The membrane 14 was fixed in the apparatus of FIG. 2 to separate the interior thereof into a 350 cc volume solution chamber 12 and a 100 cc volume vacuum chamber 13 with an effective separation surface area of 20 cm². 100 cc of the water-ethanol solution was place in the solution chamber 12 out of direct contact with the membrane 14. The separation was carried out by keeping the vacuum chamber 13 at a reduced pressure of $10^{-1}$ Torr. while heating the solution by keeping the heating bath 16 at 40° C. and cooling the membrane 14 by the cooling jacket 18 kept at 0° C., in order to recover an ethanol-rich solution from the vacuum chamber 13 by selective permeation through the membrane 14 due to the difference in the surface tensions and also in the boiling points between ethanol and water. The surface tension and the boiling point are 22.6 dyne/cm and 78.3° C. for ethanol and 72.8 dyne/cm and 100° C. for water.

EXAMPLE 2

Separation was made for a 10 wt % aqueous solution of ethanol in an identical manner as in Example 1 to recover an ethanol rich solution in the vacuum chamber except that a 60 μm thick porous polytetrafluoroethylene membrane was utilized. The membrane, which is available from Sumitomo Denko K. K., Japan under the tradename of "Fluoropore FP-010", has a critical surface tension of 28.5 dyne/cm with a porosity of 70%, and is formed with evenly distributed minute circular pores having an average diameter of 0.10 μm.

EXAMPLES 3 to 8

Separation was made for a 10 wt % aqueous solution of ethanol in an identical manner as in Example 1 to recover an ethanol rich solution in the vacuum chamber except that the solution chamber 12 was constantly supplied with an air of 25° C. at a rate of 0, 10, 20, 32, 44, and 63 ml/min, respectively.

COMPARATIVE EXAMPLE

Like separation was made for a 10 wt % aqueous solution of ethanol in an identical manner as in Example 1 to recover an ethanol rich solution in the vacuum chamber except that a non-porous polydimethylsiloxane membrane was utilized which is available from Toray Dow Corning Corp. under the tradename of "SE-9520" and shows selective permeability to ethanol in preference to water.

The ethanol-rich solutions recovered in Examples 1 to 8 and Comparative Example were analyzed to determine an ethanol concentration of the recovered solution, a permeation rate at which the solution pass through the membrane, and a separation factor $\alpha$ which is defined by the following equation:

$$\alpha = \frac{Y_{ETOH}/Y_{H_2O}}{X_{ETOH}/X_{H_2O}}$$

wherein $X_{H_2O}$ and $X_{ETOH}$ are fractions of water and ethanol respectively in aqueous ethanol solution placed in the solution chamber 12, while $Y_{H_2O}$ and $Y_{ETOH}$ are fractions of water and ethanol respectively collected in the vacuum chamber 13. As apparent from the above relation, when $\alpha$ is greater than 1, it means that ethanol has passed through the membrane 14 in a greater amount than water and therefore that ethanol is allowed to pass preferentially through the membrane to a larger extent as the value $\alpha$ becomes greater.

Thus obtained separation factor for Examples and Comparative Examples are listed in Table 2 together with the ethanol concentration in the recovered solution and the permeation rate. As seen in Table 2, the permeation rate of Examples 1 to 8 is remarkably increased as compared to those of Comparative Example, which demonstrates that ethanol can be separated at a far greater rate and therefore in a greater efficiency sufficiently for assuring industrial practicability. Further, the permeation rate as well as the ethanol concentration can be both improved in Examples 3 to 8 in which the air is being supplied to the solution chamber during the separation process.

TABLE 2

| | Supplying amount of air [ml/min] | Ethanol concentration of recovered solution [wt %] | Separation factor [α] | permeation rate [kg/m² · h] |
|---|---|---|---|---|
| Example 1 | 0 | 51.6 | 9.6 | 10.6 |
| Example 2 | 0 | 44.0 | 7.1 | 19.2 |
| Example 3 | 8 | 67.3 | 18.5 | 6.2 |
| Example 4 | 10 | 68.4 | 19.5 | 7.3 |
| Example 5 | 20 | 70.1 | 21.1 | 5.1 |
| Example 6 | 32 | 74.1 | 25.7 | 3.4 |
| Example 7 | 44 | 75.1 | 27.1 | 2.7 |
| Example 8 | 63 | 76.3 | 29.0 | 1.6 |
| Comparative Example | — | 86.2 | 56.2 | 0.008 |

Figure 3:
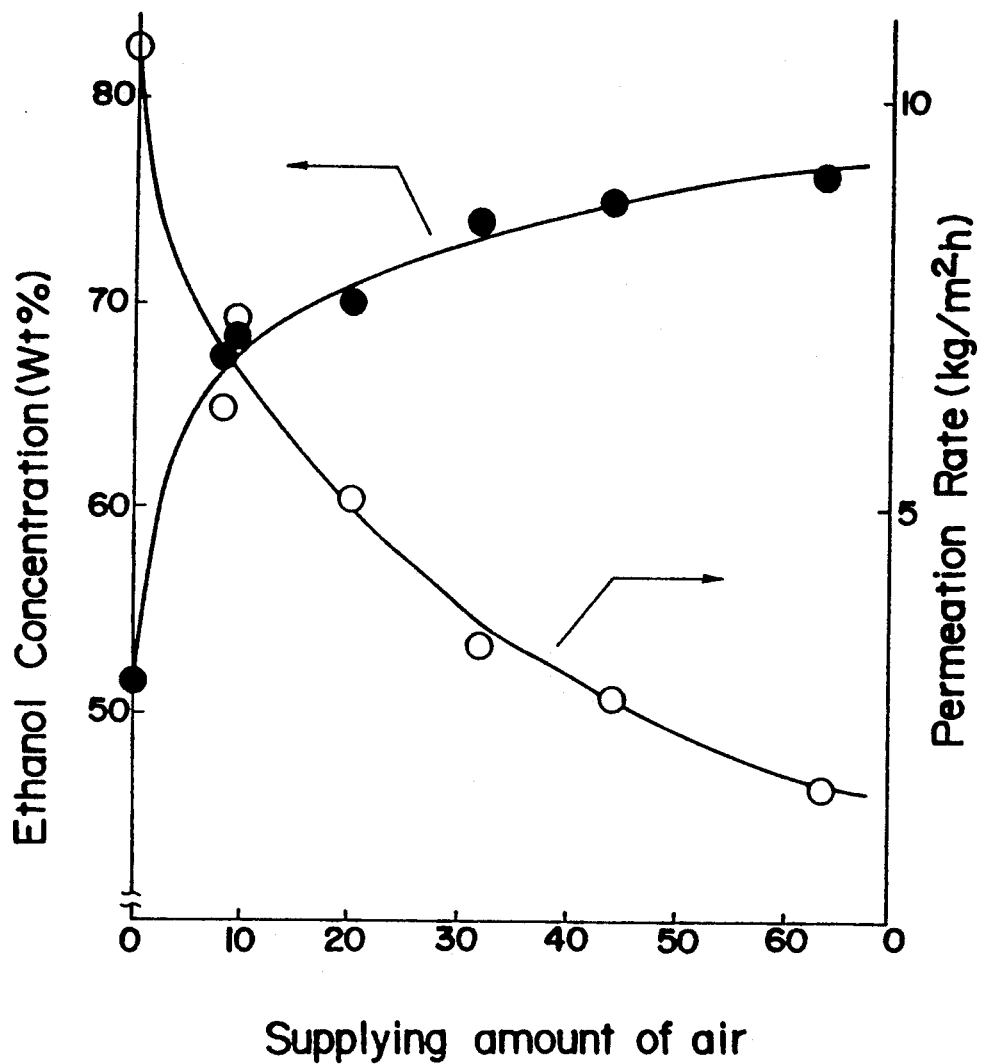
FIG. 3 is a graph illustrating separation efficiency and concentration of the permeated liquid component being separated in relation to the supplying amount of the air being introduced in a solution chamber of the apparatus.

FIG. 3 illustrates the ethanol concentration (indicated by black dots) and the permeation rate (indicated by white dots) in relation to the change in the supplying amount of the air. From this figure, it is confirmed that the ethanol concentration increases with the increase in the supplying amount of the air, but the permeation rate will decrease correspondingly. Therefore, it is required to limit the supplying amount of the air in order to well balance the concentration and the permeation rate for optimum separation efficiency.

What is claimed is:

1. A method for separating a particular liquid component from a solution containing two or more liquid components, said method comprises:

providing a vessel divided by a porous permeable membrane into a solution chamber and a vacuum chamber, said permeable membrane having an affinity stronger to said particular liquid components than to the other components;

placing said solution into said solution chamber out of direct contact with said permeable membrane; and applying a vacuum to said vacuum chamber to evaporate the solution in said solution chamber and draw the resulting vapors through said permeable membrane into said vacuum chamber in order to selectively permeate said particular component through said membrane in a vapor-to-vapor phase environment.

2. The method as set forth in claim 1, wherein said porous membrane is selected to have a critical surface tension which is closer to a surface tension of said particular component to be separated than those of the other components.

3. The method as set forth in claim 1, wherein said porous membrane is selected to have a critical surface tension which is greater than a surface tension of said particular component to be separated and is less than those of the other components.

4. The method as set forth in claim 1, wherein said porous membrane is selected to have pores of $1 \times 10^{-3}$ to 5 μm in average diameter and have a porosity of at least 5%.

5. The method as set forth in claim 1, wherein said particular component is selected to have a boiling temperature lower than those of said other components, and said membrane has a critical surface tension which is greater than a surface tension of said particular component having a lower boiling point and is less than those of the other components, and wherein said permeable membrane is cooled while heating said solution in said solution chamber.

6. The method as set forth in claim 1, wherein said solution chamber is supplied with a gas while said vacuum is applied through said membrane to said solution chamber.

* * * * *